United States Patent [19]

Lafon

[11] 4,325,964

[45] * Apr. 20, 1982

[54] PHENYLAMIDINE DERIVATIVES

[75] Inventor: Louis Lafon, Paris, France

[73] Assignee: Laboratoire L. Lafon, Maisons Alfort, France

[*] Notice: The portion of the term of this patent subsequent to Mar. 27, 1996, has been disclaimed.

[21] Appl. No.: 107,609

[22] Filed: Dec. 27, 1979

Related U.S. Application Data

[63] Continuation of Ser. No. 877,963, Feb. 15, 1978, abandoned.

[30] Foreign Application Priority Data

Feb. 15, 1977 [GB] United Kingdom .............. 06298/77
Apr. 21, 1977 [GB] United Kingdom .............. 16705/77

[51] Int. Cl.³ .................. A61K 31/36; A61K 31/155; A61K 31/19; C07C 83/10; C07C 123/00

[52] U.S. Cl. ..................................... 424/282; 424/315; 424/327; 424/326; 260/500.5 H; 260/340.5 R; 564/229

[58] Field of Search ............. 260/564 G, 500.5 H, 260/501.14, 340.5; 424/326, 315, 316, 282, 327; 564/229

[56] References Cited

U.S. PATENT DOCUMENTS 3,394,181 7/1968 Bell ....................................... 424/327
3,847,986 11/1974 Bockstahler ..................... 260/564 G
4,013,776 3/1977 Lafon ............................. 260/500.5 H
4,146,647 3/1979 Lafon ............................... 260/564 G

*Primary Examiner*—Natalie Trousof
*Assistant Examiner*—L. Hendriksen

[57] ABSTRACT

A compound having the general formula:

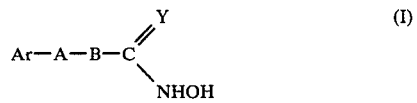

wherein Ar is an aryl group (especially an α-naphthyl, β-naphthyl or phenyl group) which may be substituted by one or more $C_{1-4}$ alkyl, $C_{1-4}$ alkoxy, methylenedioxy halogen, $CF_3$, $NH_2$ or $NO_2$ groups;

A is a —$CH_2$—, —CHOH—, —$CH_2O$—, —$CH_2S$—, —$CH_2NH$—, —$OCH_2$—, —$SCH_2$—, —NH—, —$NHCOCH_2$—, —$CH_2NHCH_2$— or —$NHCH_2$— group;

Y is O or NH; and

B is a single bond and, when A is —$CH_2$—S, may be a —$CH_2$—, or —$CH(CH_3)$— group; and their acid addition salts when Y is NH and their metal salts when Y is O.

The compounds and their salts have therapeutic utility in treatment of neuropsychic ailments.

24 Claims, No Drawings

PHENYLAMIDINE DERIVATIVES

This is a continuation, of application Ser. No. 877,963, filed Feb. 15, 1978, now abandoned.

The present invention relates to new phenyl-amidine derivatives which are useful in therapy.

According to this invention, there are now proposed, as new products which are useful in therapy, compounds having the general formula:

$$Ar-A-B-C\underset{NHOH}{\overset{Y}{\diagup\!\!\!\diagdown}} \quad (I)$$

in which:

Ar represents an aryl group (especially an α-naphthyl, β-naphthyl or phenyl group) which can be substituted by one or more $C_1-C_4$-alkyl, $C_1-C_4$-alkoxy, methylenedioxy, halogen, $CF_3$, $NH_2$ or $NO_2$ groups, A represents a $-CH_2-$, $-CHOH-$, $-CH_2O-$, $-CH_2S-$, $-CH_2NH-$, $-OCH_2-$, $-SCH_2-$, $-NH-$, $-NHCOCH_2-$, $-CH_2NHCH_2-$, or $-NHCH_2-$ group, Y represents O or NH, and B represents a single bond and can represent, if A is $CH_2S$, a $-CH_2-$ or $-CH(CH_3)-$ group, and their salts.

The term "salts" is herein understood to mean, (i) addition salts with acids, which are obtained from inorganic and organic acids when Y is NH, and (ii) metal salts, when Y is O.

The halogen atoms may be fluorine, chlorine, bromine and iodine atoms, the preferred halogens being F, Cl and Br.

Exemplary compounds according to the invention are listed in Table I below.

TABLE I $$Ar-A-B-C\underset{NHOH}{\overset{Y}{\diagup\!\!\!\diagdown}}$$

| Example | Code No. | Ar | A | B | Y | Melting point |
|---|---|---|---|---|---|---|
| 1 (a) | CRL 40514 | 2-methylphenyl | NHCH₂ | single bond | NH | 162° C. (b) |
| 2 (a) | CRL 40527 | 4-fluorophenyl | NHCH₂ | single bond | NH | 155–160° C. (b) |
| 3 | CRL 40531 | 2-bromophenyl | NHCH₂ | single bond | NH | 184° C. |
| 4 (a) | CRL 40522 | 3,4-dichlorophenyl | NHCOCH₂ | single bond | NH | 195° C. (b) |
| 5 | CRL 40410A | 4-chlorophenyl | CH₂S | CH₂ | NH | 76° C. (c) |
| 6 | CRL 40411A | 4-chlorophenyl | CH₂S | CH₂ | O | 130° C. (c) |
| 7 | CRL 40465A | 3,4-dichlorophenyl | CH₂S | CH₂ | O | 75–76° C. |
| 8 | CRL 40466A | 4-chlorophenyl | CH₂S | CH(CH₃) | O | 104–105° C. |
| 9 | CRL 40475A | α-naphthyl | CH₂S | CH₂ | O | 129–130° C. |
| 10 | CRL 40511A | 4-fluorophenyl | CH₂S | CH₂ | O | 115–116° C. |
| 11 | CRL 40498A | 4-methylphenyl | CH₂S | CH₂ | O | 107° C. |
| 12 | CRL 40515A | 3,4-dichlorophenyl | CH₂S | CH₂ | O | 116° C. |
| 13 | CRL 40516A | 2,3-dichlorophenyl | CH₂S | CH₂ | O | 124° C. |
| 14 | CRL 40539A | 4-nitrophenyl | CH₂S | CH₂ | O | 118–119° C. |

TABLE I-continued $$Ar-A-B-C{\overset{Y}{\underset{NHOH}{\nearrow}}}$$

| Example | Code No. | Ar | A | B | Y | Melting point |
|---|---|---|---|---|---|---|
| 15 | CRL 40538A | 3,4-methylenedioxyphenyl (O-CH₂-O fused) | CH₂S | CH₂ | O | 127–128° C. |
| 16 | CRL 40564A | 3,4-dimethoxyphenyl | CH₂S | CH₂ | O | 78° C. |
| 17 (a) | CRL 40492 | 2,3-dimethylphenyl | NHCH₂ | single bond | NH | 184° C. (b) |
| 18 (a) | CRL 40427 | 3-chlorophenyl | NHCH₂ | single bond | NH | 134° C. |
| 19 (d) | CRL 40457 | 4-methylphenyl | NHCH₂ | single bond | NH | 172° C. |
| 20 (d) | CRL 40477 | 3-methylphenyl | NHCH₂ | single bond | NH | 150° C. |
| 21 (a) | CRL 40478 | 2-fluorophenyl | NHCH₂ | single bond | NH | 170° C. |
| 22 (d) | CRL 40482 | 4-methoxyphenyl | NHCH₂ | single bond | NH | 154° C. |
| 23 (d) | CRL 40483 | 2-methoxyphenyl | NHCH₂ | single bond | NH | 136° C. |
| 24 (a) | CRL 40487 | 2-chlorophenyl | NHCH₂ | single bond | NH | 178° C. |

Notes
(a) hydrochloride
(b) with decomposition
(c) the corresponding hydrochloride melts at 174–176° C. with decomposition
(d) dihydrochloride The compounds of the formula I can be prepared by a method which is in itself known. The recommended methods are those described in the main Patent. Thus, derivatives of the "hydroxamic acid" type (Y=O) can be prepared according to the method I which is shown schematically by the reaction $$Ar-A-B-CO-Z_1 + NH_2OH \longrightarrow Ar-A-B-C{\overset{O}{\underset{NHOH}{\nearrow}}}$$

(where Ar, A and B are defined as above, and $Z_1$ represents Cl, Br, CH₃O, C₂H₅O, n-C₃H₇O or i-C₃H₇O).

Derivatives of the "amidoxime" type (Y=NH) can be prepared according to method II or method III which consist, respectively, of reacting a cyano derivative or an iminoalkyl ether derivative with hydroxylamine, according to the reactions $$Ar-A-B-CN + NH_2OH \longrightarrow Ar-A-B-C{\overset{NH}{\underset{NHOH}{\nearrow}}}$$

$$Ar-A-B-C{\overset{NH}{\underset{O-Alk}{\nearrow}}} + NH_2OH \longrightarrow Ar-A-B-C{\overset{NH}{\underset{NHOH}{\nearrow}}}$$

(where Alk represents a $C_1$–$C_4$-alkyl group and Ar, A and B are defined as above).

In general terms the group of hydroxamic acids and amidoximes of the formula I is prepared according to the reaction

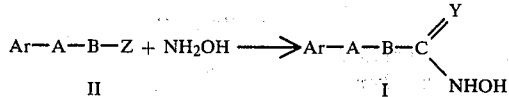

where Z represents $COZ_1$, CN or $C(=NH)O$—Alk.

The compounds II are prepared according to methods which are in themselves known.

The compounds of the formula I and their non-toxic salts are useful in therapy. They act on the central nervous system as sedatives, anxiolytic agents and muscular relaxants. In addition, certain of the compounds exhibit a hypotensive effect.

According to the invention, therapeutic compositions are recommended which contain at least one compound of the formula I, or one of its non-toxic salts, in association with a physiologically acceptable excipient.

Other advantages and characteristics of the invention will be better understood on reading the preparation examples which are described below by way of illustration.

EXAMPLE 1

2-(2-Methyl-anilino)-acetamidoxime hydrochloride

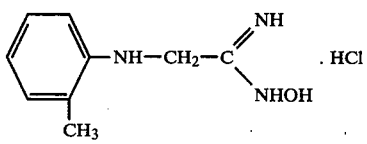

Code No.: CRL 40,514

This product is obtained with a yield of 27% according to the following reaction mechanism

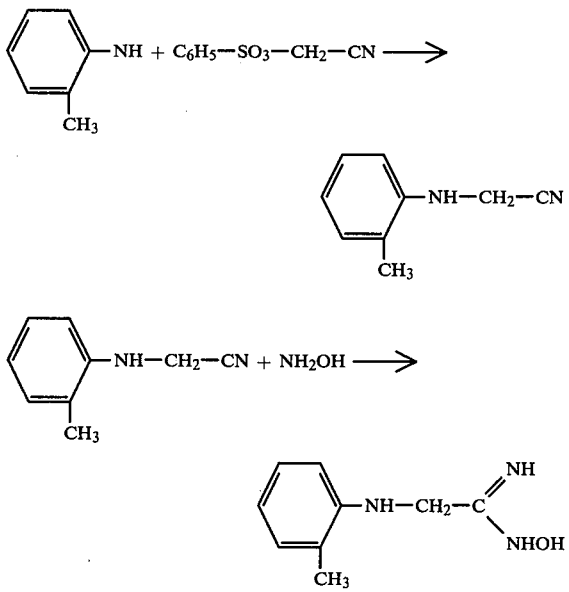

Melting point 162° C. (with decomposition)
Measured % Cl⁻: 16.93%
Theoretical % Cl⁻: 16.47%

The purity is controlled by thin layer chromatography [eluant:benzene:acetone:$NH_4OH$ (30:70:2 v/v); plate:silica gel (Merck F 254); development: U.V.+Draggendorf reagent].

EXAMPLE 2

2-(4-Fluoro-anilino)-acetamidoxime hydrochloride

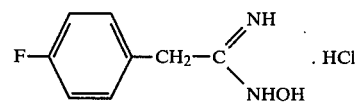

Code No. CRL 40,527

On proceeding as indicated in Example 1, but replacing the 2-methyl-aniline by 4-fluoro-aniline, the stated product is obtained with a yield of 16%.

Melting point: 155°-160° C. (with decomposition)
Measured % Cl⁻: 16.61%
Theoretical % Cl⁻: 16.17%

The purity is controlled by thin layer chromatography, as indicated in Example 1.

EXAMPLE 3

2-(2-Bromo-anilino)-acetamidoxime hydrochloride

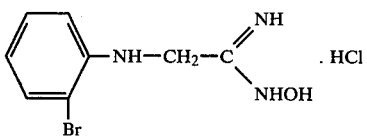

Code No. CRL 40,531

On proceeding as indicated in Example 1, but replacing the 2-methyl-aniline by 2-bromo-aniline, the stated product is obtained with a yield of 13%.

Melting point: 184° C.
Measured % Cl⁻: 12.47%
Theoretical % Cl⁻: 12.65%

The purity is controlled by thin layer chromatography, as indicated in Example 1.

EXAMPLE 4

2-(3,4-Dichloro-anilido)-acetamidoxime hydrochloride

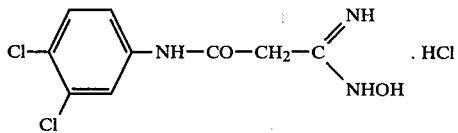

Code No. CRL 40,522

(1) N-Chloroacetyl-3,4-dichloroaniline 81 g (0.5 mol) of 3,4-dichloroaniline are dissolved 500 ml of acetone. 85 g (0.75 mol) of chloroacetyl chloride are poured in, over a period of 17 minutes, with stirring. The mixture is heated under reflux for 15 minutes, cooled and 350 ml of a 30% strength potassium carbonate solution in water (pH=8) are poured in. This solution is poured into a 2,000 ml Erlenmeyer flask and 500 ml of $H_2O$+ice are added. The precipitate which appears is filtered off, washed with water, dried and recrystallised from benzene. 102 g (yield 85%) of N-chloroacetyl-3,4-dichloroaniline are thus obtained.

(2) N-Cyanoacetyl-3,4-dichloroaniline 14.5 g (0.223 mol) of potassium cyanide are dissolved in 122 ml of H₂O. 48.50 g (0.203 mol) of the above product, dissolved in 357 ml of 95% strength ethanol, are added (dropwise over a period of 1 hour). The mixture is left stirring, at ambient temperature (15°–25° C.), overnight. The matter which is insoluble in the reaction mixture is filtered off and washed with water and with chloroform. The nitrile which is thus obtained (weight 22.2 g; yield 48%) is used in this state for the continuation of the synthesis.

The purity of the N-cyanoacetyl-3,4-dichloroaniline can be controlled by thin layer chromatography [eluant:benzene:ethanol (9:1 v/v); plate:silica gel (Merck F 254); U.V. development].

(3) CRL 40,522

A solution of 0.3 mol of hydroxylamine base in methanol is mixed with a solution of 22.2 g (0.096 mol) of the above nitrile in methanol. The reaction mixture is left at ambient temperature overnight. The medium is rendered acid with concentrated hydrochloric acid and 200 ml of H₂O are added. The methanol is evaporated off in vacuo. The residual aqueous phase is filtered and neutralised with K₂CO₃ to an alkaline pH. The neutralised aqueous phase is extracted with ether and the ether solution washed with water and dried over MgSO₄ in the presence of charcoal (3SA). The ether solution is filtered and the hydrochloride is precipitated by means of a solution of hydrogen chloride in ethanol. 5 g of CRL 40,522 are thus obtained.

Melting point: 195° C. (with decomposition)
Yield: 17%
Measured % Cl⁻: 11.41%
Theoretical % Cl⁻: 11.89%.

The purity can be controlled, as indicated in Example 1, by thin layer chromatography.

EXAMPLE 5

2-(4-Chlorobenzylmercapto)-acetamidoxime

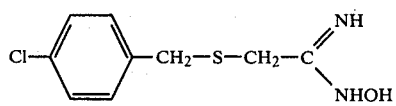

Code No.

(1) 4-Chlorobenzylmercapto-acetonitrile 13 ml (15.9 g; 0.1 mol) of 4-chlorobenzylmercaptan and a solution of 4.2 g (0.105 mol) of NaOH in 50 ml of water are mixed whilst cold. Thereafter the mixture is heated to about 60° C. and then 7.5 ml (about 1.2 mols) of chloroacetonitrile are added dropwise at this temperature. At the end of this addition (the temperature is then about 80° C.) the mixture is heated under reflux (100° C.) for 30 to 45 minutes. After cooling, the oil which has formed is extracted with ether and the aqueous phase is discarded. The ether solution is washed with dilute NaOH and then with water until the wash waters have a neutral pH. The ether phase is dried over MgSO₄ which is filtered off before the ether is evaporated. 19.7 g of the stated product are collected (yield about 100%, relative to the starting 4-chlorobenzylmercaptan); it is in the form of an oil.

(2) 2-(4-Chlorobenzylmercaptan)-acetamidoxime hydrochloride

The above product (about 0.1 mol) is taken up in 100 ml of n-butanol and the solution is mixed, whilst cold, with an aqueous solution (50 ml) of 0.2 mol (14 g) of hydroxylamine. The whole is heated at the reflux temperature of the n-butanol/water mixture, with vigorous stirring, for from 2 hours 30 minutes to 3 hours. Thereafter the butanol/water mixture is evaporated and the residue is taken up in water; the base (4-chlorobenzylmercaptoacetamidoxime) crystallises; the mixture is allowed to stand for several hours at 5°–10° C. and then the base is filtered off and dried. 19.6 g of the said base (instantaneous melting point 76° C.; yield 85%) are thus collected. The hydrochloride is prepared by dissolving the base in ether and adding a solution of hydrogen chloride in ethanol. After filtration and drying in vacuo, 21 g of the expected product are collected.

Instantaneous melting point: 174°–176° C. (with decomposition) yield: 78.5%.

EXAMPLE 6

2-(4-Chlorobenzylmercapto)-acetohydroxamic acid

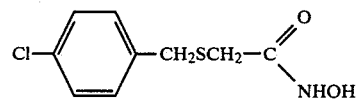

Code No. CRL (1) Anhydrous acetone (100 ml), potassium carbonate (21 g), p-chlorobenzylmercaptan (19.5 ml), methyl chloroacetate (13.2 ml) and potassium iodide (0.1 g) are mixed whilst cold. The mixture which is thus obtained is stirred and heated under reflux for 7 hours. It is then cooled, the precipitate (K₂CO₃) is filtered off, the acetone is evaporated from the filtrate and the residue is taken up in ether. The ether solution is washed with 4 N NaOH and then with water until the wash waters have a neutral pH. It is then dried over MgSO₄, the ether is evaporated off and 34.5 g (yield 100%) of methyl 2-(4-chlorobenzylmercapto)-acetate are collected in the form of a chromatographically pure oil.

(2) A solution of 0.15 mol of methyl 2-(4-chlorobenzylmercapto)-acetate in 50 ml of methanol is mixed with a solution of 0.225 mol of hydroxylamine (base) and 0.15 mol of NaOH₃ in 150 ml of methanol.

The resulting mixture is kept overnight at ambient temperature (15°–25° C.), the methanol is evaporated off and the residue is taken up in water and acidified with 3 N HCl in order to precipitate 2-(4-chlorobenzylmercapto)-acetohydroxamic acid. 31.7 g of the said acid are collected. Yield 91%; melting point about 130° C.

EXAMPLE 7

2-(3,4-Dichlorobenzylmercapto)-acetohydroxamic acid

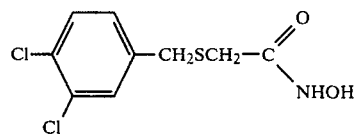

Code No. CRL (1) 3,4-Dichlorobenzylthio-acetic acid

A mixture of 19.5 (0.1 mol) of 3,4-dichlorobenzyl chloride and 7.6 g (0.1 mol) of thiourea in 50 ml of water is heated under reflux for 30 minutes, with stirring, and then, at 60°–70° C., a solution of 16 g (0.4 mol) of NaOH in 25 ml of water is run in; the mixture is heated under reflux for 15 minutes and a solution of 15 g (0.15 mol) of chloroacetic acid, 7 g of sodium carbonate and 50 ml of water are run in at 60°–70° C., and the reaction mixture is maintained under reflux for 1 hour. The mixture is acidified, whilst cold, with concentrated HCl, and is extracted with ether, and the ether extract washed with water, dried and evaporated. The residue is taken up in petroleum ether and the product filtered off. 21 g (yield 83%) of the stated product are obtained. Melting point 63°–64° C.

(2) 2-(3,4-Dichlorobenzylmercapto)-acetohydroxamic acid 20.2 g (0.08 mol) of 3,4-dichlorobenzylthioacetic acid are esterified with 10 ml of methanol, 0.6 ml of concentrated H$_2$SO$_4$ and 100 ml of dichloroethane. The mixture is heated under reflux for 4 hours, washed with water and with dilute bicarbonate and dried. The solvent is evaporated in vacuo. The oily residue is treated in methanol with a solution of hydroxylamine (0.1 mol) in the presence of 0.18 mol of sodium methylate. After leaving the reactants in contact overnight, the mixture is evaporated to dryness in vacuo, the residue is taken up in water, the solution is filtered over charcoal and the product is precipitated with 3 N HCl, the mixture is extracted with ether, the ether extract is dried, the ether is evaporated and the residue is crystallised from diisopropyl ether. 15 g (yield 71%) of the stated product are obtained; melting point: 75°–76° C.

EXAMPLE 8

2-(4-Chlorobenzylmercapto)-propionohydroxamic acid

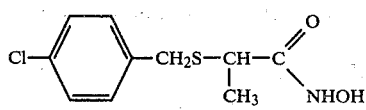

Code No. CRL (1) Ethyl 2-(4-chlorobenzylthio)-propionate

A mixture of 19.5 ml (0.15 mol) of 4-chlorobenzylmercaptan, 27.1 g (0.15 mol) of ethyl α-bromopropionate, 21 g of potassium carbonate and 0.1 g of potassium iodide in 100 ml of anhydrous acetone is maintained under reflux for 6 hours. The mixture is filtered, the precipitate is washed with acetone and the filtrate is evaporated in vacuo. 200 ml of ether are added to the residue and the ether solution is washed with dilute NaOH, dilute HCl and water.

It is then dried and evaporated in vacuo.

(2) 2-(4-Chlorobenzylmercapto)-propionohydroxamic acid 10.5 g (0.15 mol) of hydroxylamine hydrochloride are treated with a solution of sodium methylate prepared with 5.75 g (0.25 gram atom) of sodium in 200 ml of methanol. The sodium chloride is filtered off and 25.85 g (0.1 mol) of ethyl 2-(p-chlorobenzylthio)-propionate are added to the filtrate. After leaving the reactants in contact overnight, the mixture is evaporated in vacuo, the residue is taken up with 200 ml of water, the solution is filtered and the product precipitated with 3 N HCl, filtered off, washed with water and dried; 20.2 g (yield: 82%) of the stated hydroxamic acid are obtained. Melting point: 104°–105° C.

EXAMPLE 9

α-Naphthylmethylenemercapto-acetohydroxamic acid

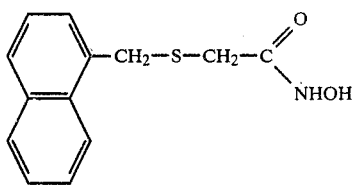

Code No. CRL (1) α-Naphthylmethylene-thioacetic acid

A solution of 15.2 g (0.2 mol) of thiourea in 100 ml of water is introduced into a 1 liter three-necked flask equipped with a magnetic stirrer, a condenser and a dropping funnel, and 35.3 g (0.2 mol) of α-chloromethyl-naphthalene are added, all at once, at 50°–60° C. The reaction mixture is heated to the reflux temperature and boiling is maintained for a quarter of an hour. The thiouronium salt precipitates. Thereafter the mixture is cooled and a solution of 32 g of sodium hydroxide (0.8 mol) in 50 ml of water is added dropwise at about 60° C. The resulting mixture is heated under reflux until the solution becomes limpid, and is cooled and a solution of about 0.28 mol of sodium chloroacetate (obtained by neutralising 26.36 g of chloroacetic acid in 200 ml of water with 23.52 g of sodium bicarbonate) is added dropwise at 60°–70° C. The whole is then heated under reflux for half an hour, cooled and acidified cold by the addition of 3 N HCl. α-Naphthylmethylene-thioacetic acid thus precipitates, and is filtered off. 44.5 g of product are collected.

(Yield: 95%). Instantaneous melting point = 102°–103° C.

(2) Ethyl α-naphthylmethylene-thioacetate 19.72 g (0.085 mol) of the above product are dissolved in 160 ml of 1,2-dichloroethane and 16 ml of anhydrous ethanol and 1.6 ml of concentrated sulphuric acid are added. The mixture is heated under reflux for at least 2 hours and cooled, the organic phase is decanted and the water formed discarded. The organic phase is washed with a dilute solution of sodium hydroxide and then with water. It is then dried over MgSO$_4$ and the solvent is evaporated. 19.8 g of ethyl α-naphthylmethylene-thioacetate [overall yield = 89%] are thus obtained, this product being in the form of a limpid orange-coloured oil.

(3) α-Naphthylmethylenemercapto-acetohydroxamic acid

The ester obtained above (0.076 mol), diluted with 50 ml of methanol, is added to a solution of hydroxylamine, prepared from 7.92 g (0.114 mol) of hydroxylamine hydrochloride in 190 ml of methanol and 4.37 g (0.19 gram atom) of sodium in 190 ml of anhydrous methanol. After leaving the reactants in contact overnight at 20° C., the methanol is evaporated, the residue is taken up in water (alkaline medium), the mixture is filtered over charcoal and acidified by adding 3 N HCl, and α-naphthylmethylene-thio-acetohydroxamic acid is thus precipitated; it is filtered off, washed with water and then with ether, and dried, 11.2 g (0.0453 mol) of the product (overall yield = 59%) are collected after recrystallisation from ethyl acetate. Instantaneous melting point = 129°–130° C.

EXAMPLE 10

2-(4-Fluorobenzylmercapto)-acetohydroxamic acid

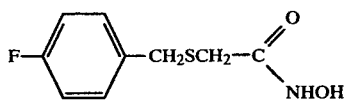

Code No. CRL (1) p-Fluorobenzylthioacetic acid

A solution of 15.2 g (0.2 mol) of thiourea in 100 ml of water is introduced into a 1 liter three-necked flask equipped with a magnetic stirrer, a condenser and a dropping funnel, and 28.9 g (0.2 mol) of p-fluorobenzyl chloride are added all at once, at 50°–60° C. The mixture is heated to reflux temperature, boiling is maintained for about 15 minutes and the solution becomes limpid. Thereafter the solution is cooled and a solution of 32 g (0.8 mol) of NaOH in water is added dropwise at about 60° C. The whole is heated under reflux for about 30 minutes, the mixture is cooled and a solution of about 0.28 mol of sodium chloroacetate (obtained by neutralising 26.46 g of chloroacetic acid in 200 ml of water with 23.52 g of sodium bicarbonate) is added dropwise at 60°–70° C. Thereafter the whole is heated under reflux for 30 minutes and then cooled. The mixture is acidified with 3 N HCl and the oil which is obtained is taken up in methylene chloride, this mixture is washed with a dilute sodium bicarbonate solution, filtered over charcoal and acidified once more with 3 N HCl; p-fluorobenzylthioacetic acid is thus precipitated, and is filtered off. After recrystallising from cyclohexane, 33.4 g (yield: 83%) of the said acid are collected. Instantaneous melting point: 68°–69° C.

(2) Ethyl p-fluorobenzylthioacetate 17 g (0.085 mol) of the acid obtained above are dissolved in 160 ml of 1,2-dichloroethane and 16 ml of anhydrous methanol and 1.6 ml of concentrated $H_2SO_4$ are added. The whole is heated under reflux for about 6 hours and then cooled, the organic phase is decanted and the water which forms is discarded, and the organic phase is washed with a dilute sodium bicarbonate solution and then with water. The solution is then dried over $Na_2SO_4$ and the solvent evaporated. 17.4 g of a yellow oil are thus collected; this is ethyl p-fluorobenzylthioacetate (overall yield 89%).

(3) 2-(4-Fluorobenzylmercapto)-acetohydroxamic acid

The ester obtained above (0.0763 mol) is added to a solution of hydroxylamine prepared from 7.92 g (0.114 mol) of hydroxylamine hydrochloride in 190 ml of methanol and 4.37 g of sodium in 190 ml of anhydrous methanol. After leaving the reactants in contact overnight at ambient temperature, the methanol is evaporated, the residue is taken up in water, the solution is filtered over charcoal and acidified with 3 N HCl and 2-(4-fluorobenzylmercapto)-acetohydroxamic acid is thus precipitated; it is filtered off and washed with water. 11.2 g (yield: 68%) of the said acid are collected. Instantaneous melting point 115°–116° C.

EXAMPLE 11

2-(4-Methoxybenzylmercapto)-acetohydroxamic acid

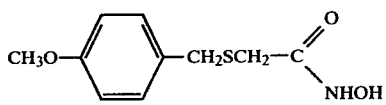

Code No. CRL (1) p-Methoxybenzylthio-acetic acid

A solution of 18.24 g (0.24 mol) of thiourea in 104 ml of 48% strength hydrobromic acid and 20 ml of water is introduced into a 1 liter three-necked flask equipped with a magnetic stirrer and a condenser. The mixture is heated at 60° C. and 27.6 g (0.2 mol) of p-methoxybenzyl alcohol are introduced. The temperature is raised to 95° C. and the mixture is allowed to cool. Crystals of the thiouronium salt appear; these are filtered off and dried. The precipitate obtained above is introduced into a 500 ml three-necked flask with 60 ml of NaOH. The mixture is heated to 70° C. and a solution of 15.6 g (0.164 mol) of chloroacetic acid dissolved in 30 ml of water is added dropwise. Thereafter the whole is heated under reflux for half an hour and then cooled. The mixture is acidified with 3 N HCl, the oil obtained is taken up in methylene chloride, and the mixture is washed with a dilute sodium bicarbonate solution, filtered over charcoal, and acidified once more with 3 N HCl in order to precipitate p-methoxybenzylthio-acetic acid. 25.7 g (yield 60%) of the said acid are collected (melting point=60° C.).

(2) Ethyl p-methoxybenzylthio-acetate 24 g (0.112 mol) of the acid obtained above are dissolved in 210 ml of 1,2-dichloroethane and 22 ml of anhydrous ethanol and 2.2 ml of concentrated sulphuric acid are added. The whole is heated under reflux for about 6 hours, cooled, the organic phase is decanted and the water which forms discarded, and the organic phase is washed with a dilute bicarbonate solution and then with water. The solution is then dried over $Na_2SO_4$ and the solvent evaporated. 26.5 g of a limpid yellow oil are thus collected; this is ethyl p-methoxybenzylthio-acetate (overall yield: 96%).

(3) 2-(4-Methoxybenzylmercapto)-acetohydroxamic acid

The above product (0.110 mol), diluted in 50 ml of methanol, is added to a solution of hydroxylamine prepared from 11.63 g (0.165 mol) of hydroxylamine hydrochloride in 275 ml of methanol and 6.32 g of sodium in 275 ml of anhydrous methanol. After leaving the reactants in contact overnight at ambient temperature, the methanol is evaporated, the residue is taken up in water, and the solution is filtered over charcoal and acidified with 3 N HCl in order to precipitate, in this way, 2-(4-methoxybenzylmercapto)-acetohydroxamic acid. After filtering off and washing with water, 19.1 g (yield 77%) of the said acid are collected. Instantaneous melting point=107° C.

EXAMPLE 12

2-(2,4-Dichlorobenzylmercapto)-acetohydroxamic acid

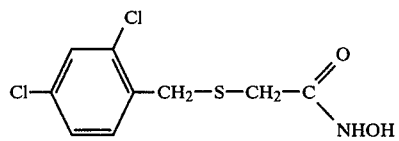

Code No. CRL (1) 2,4-Dichlorobenzylthio-acetic acid 15.2 g (0.2 mol) of thiourea in 100 ml of water are introduced into a 1 liter three-necked flask. The mixture is heated at 50°–60° C. and 39.1 g (0.2 mol) of 2,4-dichlorobenzyl chloride are added all at once. The mixture is heated to reflux and boiling is maintained for 15 minutes; the solution becomes limpid. It is then cooled and a solution of 32 g (0.8 mol) of NaOH in 50 ml of water is added dropwise at about 60° C. The mixture is again heated under reflux for 30 minutes, cooled and a solution of about 0.28 mol of sodium chloroacetate (obtained by neutralising 26.46 g of chloroacetic acid in 200 ml of water with 23.52 g of NaHCO$_3$) is added dropwise at 60°–70° C. Thereafter the whole is heated under reflux for 30 minutes, cooled, filtered and acidified with 3 N HCl; the precipitate obtained is filtered off and redissolved whilst cold in dilute bicarbonate solution, and this solution is washed with methylene chloride, filtered and acidified once more. 41.7 g (yield 83%) of the product are thus collected. Instantaneous melting point 72°–73° C.

(2) Ethyl 2,4-dichlorobenzylthio-acetate 37.65 g (0.15 mol) of the above acid are dissolved in 283 ml of 1,2-dichloroethane and 28.5 ml of anhydrous ethanol and 2.9 ml of concentrated H$_2$SO$_4$ are added. The whole is heated under reflux for 6 hours and then cooled, the organic phase is decanted and the water which forms discarded, and the organic phase is washed with a dilute bicarbonate solution and then with water. Thereafter the solution is dried over Na$_2$SO$_4$ and the solvent evaporated. 43.6 g of a yellow oil are thus collected: this is ethyl 2,4-dichlorobenzylthio-acetate (overall yield: 90%).

(3) 2-(2,4-Dichlorobenzylmercapto)-acetohydroxamic acid

The above ester (0.156 mol) is added to a solution of hydroxylamine prepared from 16.38 g (0.235 mol) of hydroxylamine hydrochloride in 300 ml of methanol and 9 g (0.391 gram atom) of sodium in 300 ml of anhydrous methanol. After leaving the reactants in contact overnight at ambient temperature, the methanol is evaporated, the residue is taken up in water, and the solution is filtered over charcoal and acidified with 3 N HCl in order to precipitate 2-(2,4-dichlorobenzylmercapto)-acetohydroxamic acid, which is filtered off and washed with water. 28 g (yield: 67%) of the said acid are collected. Instantaneous melting point: 116° C.

EXAMPLE 13

2-(2,6-Dichlorobenzylmercapto)-acetohydroxamic acid

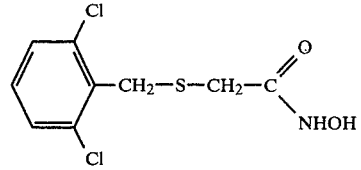

Code No. CRL

On carrying out the process as indicated in Example 12, but replacing the 2,4-(Cl$_2$)C$_6$H$_3$CH$_2$Cl with 2,6-(Cl$_2$)C$_6$H$_3$CH$_2$Cl, there are obtained successively:

(1) 2,6-dichlorobenzylthio-acetic acid (yield 83%; instantaneous melting point: 81°–82° C.), (2) ethyl 2,6-dichlorobenzylthio-acetate (yield 89%) which is in the form of a yellow oil, and (3) 2-(2,6-dichlorobenzylmercapto)-acetohydroxamic acid (yield 71%; instantaneous melting point: 124° C.).

EXAMPLE 14

2-(4-Nitrobenzylmercapto)-acetohydroxamic acid

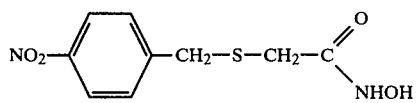

Code No. CRL (1) Ethyl 4-nitrobenzylthioacetate 43.2 g (0.2 mol) of p-nitrobenzyl bromide, 200 ml of acetone, 0.2 g of potassium iodide, 24 ml of ethyl thioglycollate (that is to say a slight excess) and 27.6 g (0.2 mol) of potassium carbonate are introduced successively into a 1 liter three-necked flask. The mixture is heated under reflux for about 4 hours until the complete disappearance of the bromo derivative; the acetone is evaporated, the oil obtained is taken up in ether and in water, the ether phase is washed with a dilute NaOH solution, so as to eliminate the excess thiol, and then with a dilute HCl solution, and is dried over Na$_2$SO$_4$, and the solvent is evaporated. 49 g (yield: 95%) of the stated product are obtained, which is in the form of an orange-coloured oil.

(2) 2-(4-Nitrobenzylmercapto)-acetohydroxamic acid

The above ester (0.156 mol), diluted in 50 ml of methanol, is added to a solution of hydroxylamine prepared from 16.38 g (0.235 mol) of hydroxylamine hydrochloride in 300 ml of methanol and 9 g (0.391 gram atom) of sodium in 300 ml of anhydrous methanol. The reactants are left in contact overnight at ambient temperature, the sodium chloride formed is filtered off, the reaction mixture is acidified immediately, the solvent is evaporated, and the precipitate obtained is taken up in water and filtered off. After recrystallisation from isopropyl alcohol, 27 g of 2-(4-nitrobenzylmercapto)-acetohydroxamic acid are obtained. Instantaneous melting point 118°–119° C.; yield 72%.

EXAMPLE 15

2-(3,4-Methylenedioxybenzylmercapto)-acetohydroxamic acid

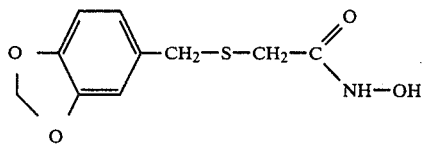

Code No. CRL (1) 3,4-Methylenedioxybenzylthio-acetic acid

A solution of 18.24 g (0.24 mol) of thiourea in 104 ml of 48% strength hydrobromic acid and 20 ml of water is introduced into a one liter three-necked flask equipped with a magnetic stirrer and a condenser. The mixture is heated to 60° C. and 30.4 g (0.2 mol) of piperonyl alcohol are introduced. The temperature is raised to 95° C. and the mixture is left to cool. Crystals of the thiouronium salt appear; these are filtered off and dried. The precipitate thus obtained is introduced into a 500 ml three-necked flask with 60 ml of sodium hydroxide solution. The mixture is heated to 70° C. and 15.6 g (0.164 mol) of chloroacetic acid in 30 ml of water are added dropwise. Thereafter the whole is heated under reflux for half an hour and then cooled. The mixture is acidified with 3 N HCl, the precipitate obtained is redissolved in a dilute bicarbonate solution, and the solution is washed with methylene chloride, filtered over charcoal and acidified once more with 3 N HCl in order to precipitate 3,4-methylenedioxybenzylthio-acetic acid, which is filtered off. After recrystallisation from a diisopropyl ether/petroleum ether mixture (1:1 v/v), 18.2 g (yield 40%) of the said acid are collected (instantaneous melting point=87° C.).

(2) Ethyl 3,4-methylenedioxybenzylthio-acetate 18.08 g (0.08 mol) of the above acid are dissolved in 160 ml of 1,2-dichloroethane and 16 ml of anhydrous ethanol and 1.6 ml of concentrated H$_2$SO$_4$ are added. The whole is heated under reflux for about 6 hours, cooled, the organic phase decanted and the water which forms discarded, and the organic phase is washed with a dilute bicarbonate solution and then with water. Thereafter the solution is dried over Na$_2$SO$_4$ and the solvent evaporated. 21 g of an orange-coloured oil are obtained: this is ethyl 3,4-methylenedioxybenzylthio-acetate (yield: 96%).

(3) 2-(3,4-Methyldioxybenzylmercapto)-acetohydroxamic acid

The above product (0.085 mol) is added to a solution of hydroxylamine prepared from 8.76 g (0.126 mol) of hydroxylamine hydrochloride in 210 ml of methanol and 4.83 g (0.21 gram atom) of sodium in 210 ml of anhydrous methanol. The reactants are left in contact overnight at ambient temperature, the methanol is evaporated, the residue is taken up in water, the solution is filtered over charcoal and acidified with 3 N HCl, and the precipitate obtained is filtered off and washed with water. 14.5 g (yield=70%) of 2-(3,4-methylenedioxybenzylmercapto)-acetohydroxamic acid are obtained. Instantaneous melting point=127°-128° C., (yield 70%).

EXAMPLE 16

2-(3,4-Dimethoxybenzylmercapto)-acetohydroxamic acid

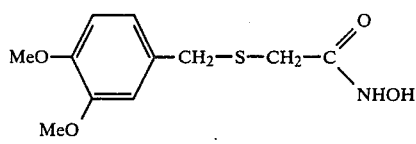

Code No. CRL (1) 3,4-Dimethoxybenzylthio-acetic acid 13.07 g (0.172 mol) of thiourea and 86 ml of water are charged into a 1 liter three-necked flask equipped with a magnetic stirrer and a condenser. The mixture is heated to 50°-60° C. and 32 g (0.172 mol) of 3,4-dimethoxybenzyl chloride are added all at once. The mixture is heated under reflux and boiling is maintained for 15 minutes; the solution becomes limpid. Thereafter the solution is cooled and a solution of 27.52 g (0.688 mol) of NaOH in 43 ml of water is added dropwise at about 60° C. The mixture is again heated under reflux for 30 minutes, cooled and a solution of sodium chloroacetate (obtained by neutralising 22.76 g of chloroacetic acid in 172 ml of water with 20.23 g of NaHCO$_3$) is added dropwise at 60°-70° C. Thereafter the whole is heated under reflux for 30 minutes, cooled and filtered and the filtrate then acidified with 3 N HCl. After recrystallisation from toluene, 28.7 g of 3,4-dimethoxybenzylthio-acetic acid are obtained. Yield: 69%. Instantaneous melting point=94° C.

(2) Methyl 3,4-dimethoxybenzylthio-acetate 24.2 g (0.1 mol) of the above acid are dissolved in 200 ml of anhydrous methanol and 4 ml of concentrated sulphuric acid are added. The whole is heated under reflux for about 3 hours, the methanol is evaporated and the oil which is obtained is taken up in ether, the organic phase is washed with a dilute sodium bicarbonate solution and then with water and dried over Na$_2$SO$_4$, and the solvent evaporated. 24.2 g (yield: 94%) of the stated product, which is in the form of an orange-coloured oil, are thus collected.

(3) 2-(3,4-Dimethoxybenzylmercapto)-acetohydroxamic acid

The above product (0.0945 mol) is added to a solution of hydroxylamine prepared from 9.95 g (0.143 mol) of hydroxylamine hydrochloride in 200 ml of methanol and from 5.45 g (0.237 gram atom) of sodium in 200 ml of anhydrous methanol. The reactants are left in contact overnight at ambient temperature, the mixture is filtered, the methanol is evaporated, the residue is taken up in water, the solution is filtered over charcoal and acidified with 3 N HCl, the oil obtained is taken up in methylene chloride, the solution is dried over Na$_2$SO$_4$, the solvent is evaporated and the residue is taken up in ethyl acetate. After filtration and washing with ether, 16.9 g (yield 70%) of the stated product are obtained. Instantaneous melting point=78° C.

EXAMPLE 17

2-(2,6-Dimethyl-anilino)-acetamidoxime hydrochloride

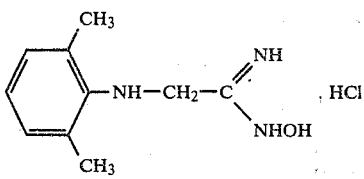

Code No. CRL 40,492

(1) Benzenesulphonate-acetonitrile ($C_6H_5SO_3$—$CH_2CN$)

104 g (1.6 mols) of potassium cyanide are dissolved in 100 ml of water. 160 g (1.6 mols) of a 30% strength formaldehyde solution are introduced at between 5° and 10° C. The mixture is stirred for 30 minutes. 212 g (1.2 mols) of benzenesulphonyl chloride are introduced dropwise at a temperature of between 10° and 20° C. The mixture is stirred at this temperature for 6 hours. The product is extracted with benzene. The benzene is washed with water. The benzene phase is decanted. Traces of water are removed by distilling the $C_6H_6.H_2O$ azeotrope. The benzene is evaporated to dryness and the residue is distilled in vacuo.

Weight = 158.5 g
Yield = 67%
Melting point = 32°–34° C.
Density = 1.3089
$n_D^{20}$ = 1.5252
Boiling point 5 mm Hg = 165°–170° C.

(2) 2-(2,6-Dimethyl-anilino)-acetonitrile

A solution of 158.5 g (0.804 mol) of benzenesulphonate-acetonitrile in 200 ml of ethyl acetate is run dropwise into a solution of 193.6 g (1.608 mols) of 2,6-dimethyl-aniline in 400 ml of ethyl acetate. The mixture is heated under reflux for 3 hours, cooled and the excess aniline benzenesulphonate is filtered off. The filtrate is evaporated to dryness. The residue is taken up in ether. Insoluble material is again filtered off and discarded. The ether is evaporated to dryness. The residue is taken up in a mixture of petroleum ether/benzene (3:4 v/v). The crystals which form are filtered off.

Weight = 84.2 g.
Yield = 65%.

(3) CRL 40,492

84.2 g (0.526 mol) of the above nitrile are dissolved in methanol and this solution is run into a solution of 2.4 mols of hydroxylamine base in methanol (this solution of hydroxylamine base having been obtained by running a solution of 129.6 g (2.4 mols) of sodium methylate in 500 ml of methanol into a solution of 166.8 g (2.4 mols) of hydroxylamine hydrochloride in 1 liter of methanol and filtering off the NaCl formed).

The mixture is stirred overnight at ambient temperature (15°–25° C.). 300 ml of water are added to the reaction mixture and the methanol is evaporated. The pH of the residual aqueous phase is adjusted to 11 with $K_2CO_3$ and the alkaline phase is extracted with ethyl acetate. The ethyl acetate is washed with 3 times 200 ml of water. The solvent is dried over $MgSO_4$ in the presence of 3 SA charcoal. The amidoxime hydrochloride is precipitated with 150 ml of a 7 N hydrogen chloride solution in ethanol. The crystals are filtered off and recrystallised from an acetone/ethanol mixture in order to obtain CRL 40,492.

Weight = 32 g
Yield = 26.4%
Melting point = 184° C. (with decomposition)
Measured % Cl$^-$ = 15.44%
Theoretical % Cl$^-$ = 15.46%.

The purity of CRL 40,492 is controlled by thin layer chromatography [eluant: $C_6H_6$/$CH_3COCH_3$/$NH_4OH$ (30:70:2 v/v); plate: silica gel (Merck F 254); development: U.V. + Draggendorf reagent].

EXAMPLE 18

2-(3-Chloro-anilino)-acetamidoxime hydrochloride

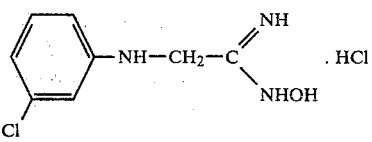

Code No. CRL 40,427

The procedure followed is as indicated in Example 13 of the main application (synthesis of CRL 40,375), replacing the 3,4-dichloro-aniline with 3-chloro-aniline. 4.2 g (yield = 4.4%) of CRL 40,427 are obtained.

Melting point = 134° C.

Analysis shows that the product obtained according to this method contains traces of 2-(3-chloroaniline)-acetamidoxime dihydrochloride, since the chlorine percentages are as follows:

Measured % Cl$^-$ = 16.37%
Theoretical % Cl$^-$ = 15.04%.

EXAMPLE 19

2-(4-Methylanilino)-acetamidoxime dihydrochloride

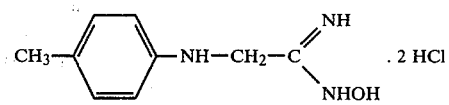

Code No. CRL 40,457

0.105 Mol of 2-(4-methylanilino)-acetonitrile in solution in methanol are treated with a solution of hydroxylamine base in methanol prepared as indicated above. The reactants are left in contact overnight at ambient temperature. Thin layer chromatography [eluant: toluene/acetone/$NH_4OH$ (30:70:2 v/v); plate: silica gel (Merck F 254); development: U.V. + Draggendorf reagent] makes it possible to demonstrate the disappearance of the nitrile and the appearance of the amidoxime. 100 ml of water are added to the reaction mixture and the methanol is evaporated. The base is extracted with ethyl acetate. The ethyl acetate is washed with water, dried over $MgSO_4$ in the presence of 3 SA charcoal and filtered. The dihydrochloride is precipitated with a hydrogen chloride solution in ethanol. CRL 40,457 is obtained by recrystallisation from an acetone/ethanol mixture (1:1 v/v).

Weight = 5.65 g
Yield = 22%
Melting point = 172° C.
Measured % Cl$^-$ = 28.42%

Theoretical % Cl$^-$ = 28.17%.

EXAMPLE 20

2-(3-Methylanilino)-acetamidoxime dihydrochloride

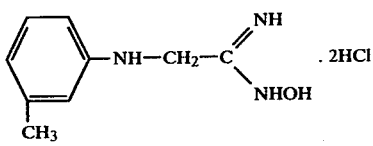

Code No. CRL 40,477

The procedure followed is as indicated in Example 19, replacing the 2-(4-methylanilino)-acetonitrile with 0.105 mol of 2-(3-methylanilino)-acetonitrile. CRL 40,477 is obtained by recrystallisation from an ethyl acetate/ethanol mixture (the recrystallisation is aided by the addition of petroleum ether to the ethyl acetate/ethanol mixture).
Weight = 12 g
Yield = 15%
Melting point = 150° C.
Measured % Cl$^-$ = 27.80%
Theoretical % Cl$^-$ = 27.77%.

EXAMPLE 21

2-(2-Fluoroanilino)-acetamidoxime hydrochloride

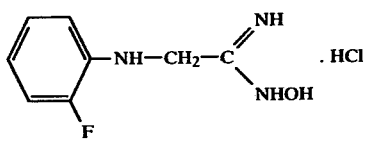

Code No. CRL 40,478

A solution of 59.1 g of benzenesulphonate-acetonitrile is run into a solution of 66.6 g (0.6 mol) of 2-fluoroaniline in 300 ml of ethyl acetate. The mixture is heated under reflux for 3 hours. The insoluble matter (2-fluoroaniline benzenesulphonate) is filtered off and the ethyl acetate is evaporated. The resulting residue is treated with a solution of 0.6 mol of hydroxylamine base in methanol, prepared as indicated above.

The mixture is allowed to stand overnight at ambient temperature (15°-25° C.). 100 ml of water are added and that methanol is evaporated. The aqueous phase is extracted with ethyl acetate. The solvent is washed with water, decanted, and is dried over MgSO$_4$ in the presence of 3 SA charcoal. The insoluble matter is filtered off. The hydrochloride is precipitated with a solution of hydrogen chloride in ethanol. The crystals are recrystallised from an ethyl acetate/ethanol mixture using petroleum ether to facilitate the crystallisation.

CRL 40,478 is thus obtained.
Weight = 5 g
Yield = 7.5%
Melting point = 170° C.
Measured % Cl$^-$ = 16.54%
Theoretical % Cl$^-$ = 16.17%.

The purity can be checked by thin layer chromatography [eluant:toluene/acetone/NH$_4$OH 30:70:2 v/v); plate: silica gel (Merck F 254); development: U.V.+-Draggendorf reagent].

EXAMPLE 22

2-(4-Methoxyanilino)-acetamidoxime dihydrochloride

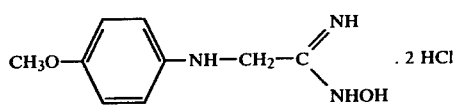

Code No. CRL 40,482

The procedure is followed as indicated in Example 21, replacing the 2-fluoroaniline with 0.2 mol of 4-methoxyaniline. CRL 40,482 is thus obtained.
Weight = 5 g
Yield = 20%
Melting point = 154° C.
Measured % Cl$^-$ = 26.04%
Theoretical % Cl$^-$ = 26.49%.

The purity can be checked by thin layer chromatography [eluant:benzene/acetone/NH$_4$OH (30:70:2 v/v); plate: silica gel (Merck F 254); development: U.V.+-Draggendorf reagent].

EXAMPLE 23

2-(2-Methoxy-anilino)-acetamidoxime dihydrochloride

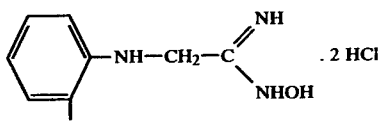

Code No. CRL 40,483

The procedure followed is as indicated in Example 21, replacing the 2-fluoro-aniline with 2-methoxy-aniline. 4.5 g (yield = 10%) of CRL 40,483 are obtained by recrystallisation from an acetone/ethanol mixture (1:1 v/v).

The purity can be checked as indicated in Example 22.

EXAMPLE 24

2-(2-Chloroanilino)-acetamidoxime hydrochloride

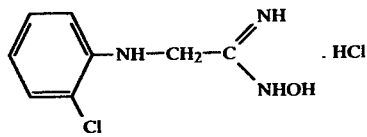

Code No. CRL 40,487

The procedure followed is as indicated in Example 21, replacing the 2-fluoro-aniline with 2-chloro-aniline. 5 g (yield = 10%) of CRL 40,487 are thus obtained.

The purity can be checked as indicated in Example 22.

The pharmacological tests which have been carried out with the compounds according to the invention have made it possible to show their action on the central nervous system. More precisely, the products of the formula I are sedatives, anxiolytic agents and/or muscular relaxants. Moreover, CRL 40,522 (the product of Example 4) exhibits, in addition to these actions on the central nervous system, a hypotensive effect at a dose of 50 mg/kg (administered orally in aqueous solution at a concentration of 5 g/l of CRL 40,522) in genetically hypertensive rats. The reduction in arterial pressure is about 17% and the hypotensive effect disappears 24 hours after administration of the product.

The compounds are thus indicated for treatment of neuropsychic ailments.

We claim:

1. A chemical compound selected from the group consisting of:
   I. The following acetamido oximes and the non-toxic acid addition salts thereof:
   2-(4-fluoro-anilino)-acetamidoxime,
   2-(2-bromo-anilino)-acetamidoxime,
   2-(3,4-dichloro-anilino-acetamidoxime,
   2-(4-chlorobenzylmercapto)-acetamidoxime,
   2-(3-chloro-anilino)-acetamidoxime,
   2-(4-methyl-anilino)-acetamidoxime,
   2-(3-methyl-anilino)-acetamidoxime,
   2-(2-fluoro-anilino)-acetamidoxime,
   2-(4-methoxy-anilino)-acetamidoxime,
   2-(2-methoxy-anilino)-acetamidoxime,
   2-(2-chloro-anilino)-acetamidoxime; and
   II. The following hydroxamic acids and the non-toxic metallic salts thereof:
   2-(4-chlorobenzylmercapto)-acetohydroxamic acid,
   2-(3,4-dichlorobenzylmercapto)-acetohydroxamic acid,
   2-(4-chlorobenzylmercapto)-propionohydroxamic acid,
   d-naphthylmethylenemercapto-acetohydroxamic acid,
   2-(4-fluorobenzylmercapto)-acetohydroxamic acid,
   2-(4-methoxybenzylmercapto)-acetohydroxamic acid,
   2-(2,4-dichlorobenzylmercapto)-acetohydroxamic acid,
   2-(2,6-dichlorobenzylmercapto)-acetohydroxamic acid,
   2-(4-nitrobenzylmercapto)-acetohydroxamic acid,
   2-(3,4-methylenedioxybenzylmercapto)-acetohydroxamic acid,
   2(3,4-dimethoxybenzylmercapto)-acetohydroxamic acid.

2. A compound according to claim 1, namely 2-(4-fluoro-anilino)-acetamidoxime hydrochloride.

3. A compound according to claim 1, namely 2-(2-bromo-anilino)-acetamidoxime hydrochloride.

4. A compound according to claim 1, namely 2-(3,4-dichloro-anilido)-acetamidoxime hydrochloride.

5. A compound according to claim 1, namely 2-(4-chlorobenzylmercapto)-acetamidoxime.

6. A compound according to claim 1, namely 2-(4-chlorobenzylmercapto)-acetohydroxamic acid.

7. A compound according to claim 1, namely 2-(3,4-dichlorobenzylmercapto)-acetonhydroxamic acid.

8. A compound according to claim 1, namely 2-(4-chlorobenzylmercapto) propionohydroxamic acid.

9. A compound according to claim 1, namely d-naphthylmethylenemercapto-acetohydroxamic acid.

10. A compound according to claim 1, namely 2-(4-fluorobenzylmercapto)-acetohydroxamic acid.

11. A compound according to claim 1, namely 2-(4methoxybenzylmercapto)-acetohydroxamic acid.

12. A compound according to claim 1, namely 2-(2,4-dichlorobenzylmercapto)-acetohydroxamic acid.

13. A compound according to claim 1, namely 2-(2,6-dichlorobenzylmercapto)-acetohydroxamic acid.

14. A compound according to claim 1, namely 2-(4-nitrobenzylmercapto)-acetohydroxamic acid.

15. A compound according to claim 1, namely 2-(3,4-methylenedioxybenzyl mercapto)-acetohydroxamic acid.

16. A compound according to claim 1, namely 2-(3,4-dimethoxybenzylmercapto)-acetohydroxamic acid.

17. A compound according to claim 1, namely 2-(3-chloro-anilino)-acetamidoxime hydrochloride.

18. A compound according to claim 1, namely 2-(4-methyl-anilino)-acetamidoxime dihydrochloride.

19. A compound according to claim 1, namely 2-(3-methyl-anilino)-acetamidoxime dihydrochloride.

20. A compound according to claim 1, namely 2-(2-fluoro-anilino)-acetamidoxime hydrochloride.

21. A compound according to claim 1, namely 2-(4-methoxy-anilino)-acetamidoxime dihydrochloride.

22. A compound according to claim 1, namely 2-(2-methoxy-anilino)-acetamidoxime dihydrochloride.

23. A compound according to claim 1, namely 2-(2-chloro-anilino)-acetamidoxime hydrochloride.

24. A therapeutic composition comprising a physiologically acceptable excipient and a pharmaceutically effective amount of a compound selected from the group consisting of the compounds set forth in claim 1 and the non-toxic acid addition and metallic salts thereof, said composition being useful for sedative and anxiolytic purposes.

* * * * *